(12) United States Patent
Menard (10) Patent No.: US 7,103,344 B2
(45) Date of Patent: Sep. 5, 2006

(54) DEVICE WITH PASSIVE RECEIVER

(76) Inventor: Raymond J. Menard, 906 E. First St., Hastings, MN (US) 55033

( * ) Notice: Subject to any disclaimer, the term of this patent is extended or adjusted under 35 U.S.C. 154(b) by 592 days.

(21) Appl. No.: 10/285,778

(22) Filed: Nov. 1, 2002

(65) Prior Publication Data

US 2003/0119568 A1    Jun. 26, 2003

Related U.S. Application Data

(63) Continuation-in-part of application No. 10/165,624, filed on Jun. 7, 2002, now abandoned.

(51) Int. Cl.
*H04B 1/16* (2006.01)

(52) U.S. Cl. ............... 455/343.2; 455/574; 455/41.2; 455/552.1

(58) Field of Classification Search ........... 455/41.1–2, 455/550.1, 552.1, 574, 343.1–6, 553.1, 90.1–3; 370/311; 340/10.1, 10.33–34
See application file for complete search history.

(56) References Cited

U.S. PATENT DOCUMENTS

| | | | |
|---|---|---|---|
| 3,843,841 A | 10/1974 | Rubinstein | |
| 3,969,709 A | 7/1976 | Isaacs et al. | |
| 4,237,344 A | 12/1980 | Moore | |
| 4,284,849 A | 8/1981 | Anderson et al. | |
| 4,303,801 A | 12/1981 | Anderson et al. | |
| 4,531,527 A | 7/1985 | Reinhold, Jr. | |
| 4,772,876 A | 9/1988 | Laud | |
| 4,843,377 A | 6/1989 | Fuller et al. | |
| 4,856,047 A | 8/1989 | Saunders | |
| 4,908,600 A | 3/1990 | Martinez | |
| 4,993,059 A | 2/1991 | Smith et al. | |
| 4,994,787 A | 2/1991 | Kratt et al. | |
| 5,016,172 A | 5/1991 | Dessertine | |
| 5,025,374 A | 6/1991 | Roizen et al. | |
| 5,062,147 A | 10/1991 | Pickett | |
| 5,081,667 A | 1/1992 | Ze'ev Drori et al. | |
| 5,128,979 A | 7/1992 | Reich et al. | |
| 5,179,571 A | 1/1993 | Schilling | |
| 5,195,126 A | 3/1993 | Carrier et al. | |
| 5,223,844 A | 6/1993 | Mansell et al. | |
| 5,228,449 A | 7/1993 | Christ et al. | |
| 5,245,346 A * | 9/1993 | Nishimura et al. | ........... 342/42 |

(Continued)

FOREIGN PATENT DOCUMENTS

DE    19962915 A1    9/2001

(Continued)

OTHER PUBLICATIONS

Bluetooth Product Design—a natural progression of our existing business,;RTX; 4 pgs.

(Continued)

*Primary Examiner*—Matthew Anderson
*Assistant Examiner*—Tuan Tran
(74) *Attorney, Agent, or Firm*—Gerald E. Helget; Nelson R. Capes; Briggs & Morgan, P.A.

(57) ABSTRACT

A wireless communications apparatus includes a wake-up receiver adapted to receive a wake-up signal and an initially powered-off, sleeping wireless communications transceiver. When the wake-up receiver receives the wake-up signal, it can in turn power on the wireless communications transceiver. In another aspect, the invention includes an apparatus for sending a wake-up signal to the wake-up receiver. The wake-up transmitter and the wake-up receiver can communicate via a variety of wireless communications protocols, including the BLUETOOTH™ standard.

23 Claims, 6 Drawing Sheets

U.S. PATENT DOCUMENTS

| | | | |
|---|---|---|---|
| 5,276,728 A | | 1/1994 | Pagliaroli et al. |
| 5,278,539 A | | 1/1994 | Lauterbach et al. |
| 5,319,355 A | | 6/1994 | Russek et al. |
| 5,319,698 A | | 6/1994 | Glidewell |
| 5,333,173 A | | 7/1994 | Seazholtz et al. |
| 5,345,231 A | * | 9/1994 | Koo et al. ............. 340/870.31 |
| 5,351,235 A | | 9/1994 | Lahtinen |
| 5,390,238 A | | 2/1995 | Kirk et al. |
| 5,398,782 A | | 3/1995 | Talbot |
| 5,402,466 A | | 3/1995 | Delahanty |
| 5,404,577 A | | 4/1995 | Zuckerman et al. |
| 5,412,372 A | | 5/1995 | Parkhurst et al. |
| 5,416,695 A | | 5/1995 | Stutman et al. |
| 5,432,841 A | | 7/1995 | Rimer |
| 5,451,839 A | | 9/1995 | Rappaport et al. |
| 5,485,504 A | | 1/1996 | Ohnsorge |
| 5,513,111 A | | 4/1996 | Wortham |
| 5,565,858 A | * | 10/1996 | Guthrie ................... 340/10.33 |
| 5,568,535 A | | 10/1996 | Sheffer et al. |
| 5,570,083 A | | 10/1996 | Johnson |
| 5,583,831 A | | 12/1996 | Churchill et al. |
| 5,587,701 A | | 12/1996 | Hess |
| 5,630,207 A | | 5/1997 | Gitlin et al. |
| 5,640,147 A | | 6/1997 | Chek et al. |
| 5,652,564 A | | 7/1997 | Winbush |
| 5,652,570 A | | 7/1997 | Lepkofker |
| 5,687,215 A | | 11/1997 | Timm et al. |
| 5,712,619 A | | 1/1998 | Simkin |
| 5,719,551 A | | 2/1998 | Flick |
| 5,736,932 A | | 4/1998 | Bulfer et al. |
| 5,739,748 A | | 4/1998 | Flick |
| 5,742,233 A | | 4/1998 | Hoffman et al. |
| 5,752,976 A | | 5/1998 | Duffin et al. |
| 5,754,111 A | | 5/1998 | Garcia |
| 5,777,551 A | | 7/1998 | Hess |
| 5,784,685 A | | 7/1998 | Stanford et al. |
| 5,786,746 A | | 7/1998 | Lombardo et al. |
| 5,793,283 A | | 8/1998 | Davis |
| 5,812,536 A | | 9/1998 | Manduely |
| 5,815,417 A | | 9/1998 | Orr et al. |
| 5,821,854 A | | 10/1998 | Dorinski et al. |
| 5,825,283 A | | 10/1998 | Camhi |
| 5,845,203 A | | 12/1998 | LaDue |
| 5,850,180 A | | 12/1998 | Hess |
| 5,850,344 A | | 12/1998 | Conkright |
| 5,852,408 A | | 12/1998 | Christiansen et al. |
| 5,870,020 A | | 2/1999 | Harrison, Jr. |
| 5,870,673 A | * | 2/1999 | Haartsen .................. 455/426.1 |
| 5,873,043 A | | 2/1999 | Comer |
| 5,874,889 A | | 2/1999 | Higdon et al. |
| 5,892,442 A | | 4/1999 | Ozery |
| 5,894,591 A | | 4/1999 | Tamayo |
| 5,898,391 A | | 4/1999 | Jefferies et al. |
| 5,898,904 A | | 4/1999 | Wang |
| 5,902,234 A | | 5/1999 | Webb |
| 5,907,279 A | | 5/1999 | Bruins |
| 5,917,405 A | | 6/1999 | Joao |
| 5,933,080 A | | 8/1999 | Nojima |
| 5,959,529 A | | 9/1999 | Kail, IV |
| 5,995,839 A | * | 11/1999 | Coursey et al. ............. 455/445 |
| 6,023,223 A | | 2/2000 | Baxter, Jr. |
| 6,023,241 A | | 2/2000 | Clapper |
| 6,028,514 A | | 2/2000 | Lemelson et al. |
| 6,035,021 A | | 3/2000 | Katz |
| 6,044,257 A | | 3/2000 | Boling et al. |
| 6,046,687 A | * | 4/2000 | Janky ........................ 340/988 |
| 6,057,758 A | | 5/2000 | Dempsey et al. |
| 6,087,952 A | | 7/2000 | Prabhakaran |
| 6,118,866 A | | 9/2000 | Shtivelman |
| 6,288,641 B1 | | 9/2001 | Casais |
| 6,295,346 B1 | | 9/2001 | Markowitz et al. |
| 6,340,928 B1 | | 1/2002 | McCurdy |
| 6,388,612 B1 | | 5/2002 | Neher |
| 6,498,923 B1 | * | 12/2002 | Ikefuji et al. ............. 455/41.1 |
| 6,571,103 B1 | * | 5/2003 | Novakov .................... 455/464 |
| 6,668,216 B1 | * | 12/2003 | Mays ......................... 701/19 |
| 6,760,578 B1 | * | 7/2004 | Rotzoll .................... 455/343.2 |

FOREIGN PATENT DOCUMENTS

| | | |
|---|---|---|
| WO | WO 01/26335 A3 | 4/2001 |
| WO | WO 01/47597 A2 | 7/2001 |

OTHER PUBLICATIONS

Your Vision—Our Solution; RTX Telecom; 5 pgs.
Lucent Technologies and Bluetooth; Lucent Technologies, Inc.; Dec. 1999; 2 pgs.
Houston, Jerry; Socket Teams with Cambridge Silicon Radio for Bluetooth Cordless Networking on Windows CE; Socket Communications, Inc., 1999; 2 pgs.
Technology Solutions for Bluetooth; Ericsson Microelectronics; Nov. 1999; 2 pgs.
The Secret of Success!, Signal Newletter No. 3—The Official Newsletter of the Bluetooth Special Interest Group; Nov. 1999; 8 pgs.
Unleash the World—Core Technology for Bluetooth applications; Ericsson Mobile Communications AB, 1999; 7 pgs.
Wireless Connections Made Easy; Bluetooth; 19 pgs.
Get a better vantage point and outmaneuver the competition; Cadence Design Systems, Inc.; 1999; 2 pgs.
Empowering the mobile enterprise; Puma Technology, Inc.; 1996-1999; 2 pgs.
Designing Solutions for the Internet Economy, Intel Developer Forum Spring 2000; Feb. 15-17, 2000; 2 pgs.
Socket's Bluetooth Cordless Communications Card; Socket Communications, Inc.; Dec. 1999; 2 pgs.
Nobel, Carmen; Microsoft jumps on Bluetooth bandwagon; PC Week; Dec. 6, 1999; 1 pg.
CreataLink; Motorola, Inc., 1999; 2 pgs.
Bluetooth White Paper; AU-System AB; 1999; entire pamphlet.
Object Geode—The Most Advanced Integrated Environment for the Development of Distributed Real-time Systems; Veriolog S.A.; 1998; entire brochure.
Bluetooth—solutions for personal area networking; TDK Systems, Inc.; 4 pgs.
Diganswer Bluetooth—Development and Demonstration Tools Product Sheet; DIGIANSWER A/S; 6 pgs.
The Ericsson Bluetooth Development Kit, Ericsson Mobile Communications, AB; 1999; 2 pgs.
Bluetooth Blue-Share Product Brief; ACER NeWeb Corporation; 1 pg.
Blue-Connect Product Brief; ACER NeWeb Corporation; 1 pg.
Bluetooth Development using SDL, MSC and TTCN; Telelogic AB; 13 pgs.
Emulation System Speeds Development of CDMA Satcom Handsets; Penton Publishing, Inc.; 1997; 4 pgs.
Diganswer/Bluetooth Technology; DIGIANSWER (lrl) Ltd.; 8 pgs.
ARM9 Thumb Family; Arm Ltd.; 6 pgs.
Enabling Innovation; Arm Ltd.; 1999; 10 pgs.
Arm7 Thumb Family; Arm Powered; 4 pgs.
IVT—Bluetooth Protocol Stack SDL/C Source Code; Bluetooth; 2 pgs.
Spontaneous Connections; CommVerge; May 2000; 6 pgs.
OSE—the new generation realtime operating system; ENA OSE Systems; 1999; entire booklet.
Alarmnet-M Mobitex System; ArlamNet; 2000; 1 pg/.
AlarmNet-C Control Channel Cellular; AlarmNet; 2000; 2 pgs.
Samsung Electronics Joins Home Radio Frequency Group in Development of Wireless Network for the Home; Samsung Electronics, 1998; pp. 1-2.
Tachless Remote Engine Starters; ALMEX, 2000; pp. 1-3.
Introduction to the HomeRF Technical Specification; HomeRF; 2000; pp. 1-17.

Posti, J.; Motorola Introduces CreataLink 2 XT two-way data transceiver; Motorola Press Release; Mar. 1999; 2 pgs.

CreataLink 2XT; Motorola Messaging Products; Mar. 1999; 1 pg.

CreataLink 2XT; Motorola; Nov. 2000; 1 pg.

Skyroute Wireless Communications; 1974; pp. 1-4.

21st Century Emergency Safety Communications Policy; ComCARE Alliance; 2000; pp. 1-3.

allNetDevices:—Geoworks, Openwave End Patent Fight; allNetDevices; 2000; 1 pg.

Automatic Crash Notification, ComCARE Alliance; 2000; 2 pgs.

Connect 24 Data Communications; Connect 24; 2001; 1 pg.

Emergency 911 Cellular Phone and Cellular Phone Accessories; AAA Communications; 2001; 7 pgs.

Glossary: ComCARE Alliance; 2000; 3 pgs.

PSAP Updates and Third-Party Call Centers; ComCARE Alliance; 2000; 2 pgs.

Will the push—not pull—of Internet information dramatically alter our Web interactions?; Sunworld; 2000; 6 pgs.

ORA Electronics Introduces Rescue Mate, a Complete Cellular Telephone Safety Package; Hands-Free Operation, Instant Emergency 911 Access, Roadside Assistance Services; Business Wire; 1998; 2 pgs.

allNetDevices:—The Device-Centric Home in 2000: Close, But No Cigar; Dec. 26, 2000; 3 pgs.

AlarmNet-A Original AlarmNet; Dec. 27, 2000; 2 pgs.

* cited by examiner

DEVICE WITH PASSIVE RECEIVER

The present application is a continuation-in-part of co-pending U.S. patent application Ser. No. 10/165,624, filed Jun. 7, 2002, and claims the benefit of International Application No. PCT/US01/18734, filed Jun. 8, 2001.

FIELD OF THE INVENTION

The present invention relates generally to wireless networks and in particular to an apparatus and method to activate a wireless device that is powered off.

BACKGROUND OF THE INVENTION

Wireless networks may be used to transmit signals from devices that are only activated rarely. For example, a sensor detecting glass-breakage in a security alarm system may only rarely be activated. In such a design, the system may continuously power the sensor and processor to monitor for glass breakage while the associated wireless transceiver may be powered-down to save battery power. Upon detecting glass breakage, the sensor/processor module can power up the associated wireless transceiver and use it to transmit signals associated with the detected event to a central control panel. This works to "wake up" the transceiver from within the device. But how could the control panel query the status of the glass breakage detector since its transmitter is normally in the off state—that is, "wake up" the transceiver from outside the device?

Such a dilemma increases in importance in the case of implanted devices. Consider for example an implanted medical device such as a combination heart monitor/defibrillator that is implanted in a person's body. In like manner to the previous example, the heart monitor could "wake up" a powered-down associated transceiver upon detecting a dangerous heart condition or a heart attack. But how could a medical professional access the heart monitor when the transceiver is in the powered-down state?

In the art are known systems to manage the power condition of the transceiver and yet make it available to receive external requests. For example, the transceiver may power up on a schedule and check for messages. The schedule may be synchronized with the associated network or it may be intrinsic only to the transceiver itself. This scheduling approach allows the transceiver to be shut down most of the time and so conserve precious battery power. There are at least two problems with this method. First, the transceiver is still being powered-up; using what is often critical battery power. Indeed, in some transceiver systems, the receiving component draws more power than the transmitting component. Second, some wireless networks require acquisition time for the network to synchronize, handshake, verify security protocols, etc. This can be a time consuming and by correlation, a power consuming process. For many devices that may be associated with wireless networks, this is an unacceptable solution because the power draw cannot be supported.

U.S. Pat. Nos. 5,115,236, 5,553,058, and 5,973,611 show the use of signals to remotely wake up a receiver. U.S. Pat. Nos. 3,145,380 and 4,963,887 show the use of transmitted radio frequency energy to provide energy to a responder system.

What is needed in the art is a system to activate a transceiver, such system requiring little or no power draw of its own. In addition, it is preferable that the activation signal be transmitted on a network (i.e., frequency or data communications protocol) distinct from the primary network used by the receiver to be activated.

SUMMARY

One skilled in the art will readily recognize that the embodiments described solve all of these problems and many more not mentioned expressly herein.

A significant advantage of the present invention is that it provides non-contact, non-line-of-sight operation that can activate a transceiver that is powered-down.

This summary is intended to provide a brief overview of some of the embodiments of the present system, and is not intended in an exclusive or exhaustive sense, and the scope of the invention is to be determined by the attached claims and their equivalents.

In one embodiment disclosed herein is a method to use radio frequency energy to activate a primary transceiver that is normally inactive or powered off. An electromagnetic field is used to excite a nearby antenna and its associated companion receiver or transceiver and optionally its processing and memory circuits. Based upon the energy received and data that may be carried in the electromagnetic energy field by this companion communications system, another more robust primary transceiver system is activated for communications. In addition, the data sent and received in the companion system may carry identification information, security checks, or instructions.

DETAILED SYSTEM DESCRIPTION

This detailed description provides a number of different embodiments of the present system. The embodiments provided herein are not intended in an exclusive or limited sense, and variations may exist in organization, dimension, hardware, software, mechanical design and configuration without departing from the claimed invention, the scope of which is provided by the attached claims and equivalents thereof.

The present system provides many benefits, including but not limited to those described. Many other benefits will be appreciated by those skilled in the art upon reading and understanding the present description.

U.S. patent application Ser. No. 10/165,624 filed Jun. 7, 2002 is hereby incorporated by reference in its entirety.

About the Transmission of Radio Frequency Energy

The present invention involves the transmission of energy and data wirelessly using radio frequencies. There are two primary methods of doing this as displayed in FIG. 1A and FIG. 1B. They are inductive coupling and propagation coupling.

Figure 1A:
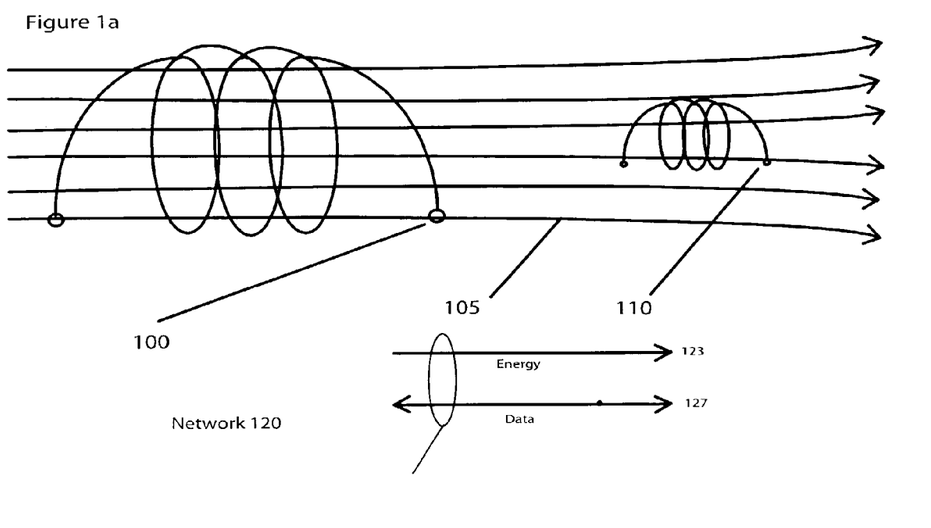
FIG. 1A is a diagram depicting inductive transference of energy and data (coupling) between two antenna coils.

FIG. 1A depicts an example of inductive coupling otherwise known as magnetic coupling. Coil 100, which can be considered a type of an antenna, has voltage applied to it, which induces magnetic field 105. Coil 110 placed in the magnetic field 105 has voltage induced into it by the effect of the magnetic field 105. This induced voltage can be used to drive circuits attached to coil 110 with or without any other source of power and thus there is transference of radio frequency energy (RFE) 123. The device associated with coil 110 is often known as a 'transponder', that is, transmit-respond, because the energy can drive a response transmission. In addition, applying fluctuations to the voltage and current on coil 100, causes corresponding fluctuations in the magnetic field. To carry data efficiently between the two coils 100 and 110 requires the data to be superimposed upon a rhythmically varying field. This rhythm is known as a sinusoidal wave and is the carrier wave for the data. By altering one of the three primary aspects of the wave, including its amplitude, its frequency, or its phase, the data can be transferred. These methods are known respectively as amplitude shift keying (ASK), frequency shift keying (FSK) and phase shift keying (PSK). Although these three are the primary methods, there are more than a dozen various methods to carry data in the electromagnetic wave. In addition, there are multiple access methods, such as CDMA, WCDM, TDMA, FDMA and many others. These access methods are strategies to put more data in the same bandwidth. Therefore, data 127 from coil 100 to coil 110 can be transferred in the field 105, as well as RFE 123. By using energy 123 or an alternate source of energy, data from coil 110 can be returned to coil 100. Thus the flow of data can be bi-directional. If coil 110 has no source of energy except field 105, it is said to be passive. If it has an additional source of energy, it is said to be active.

Figure 1B:
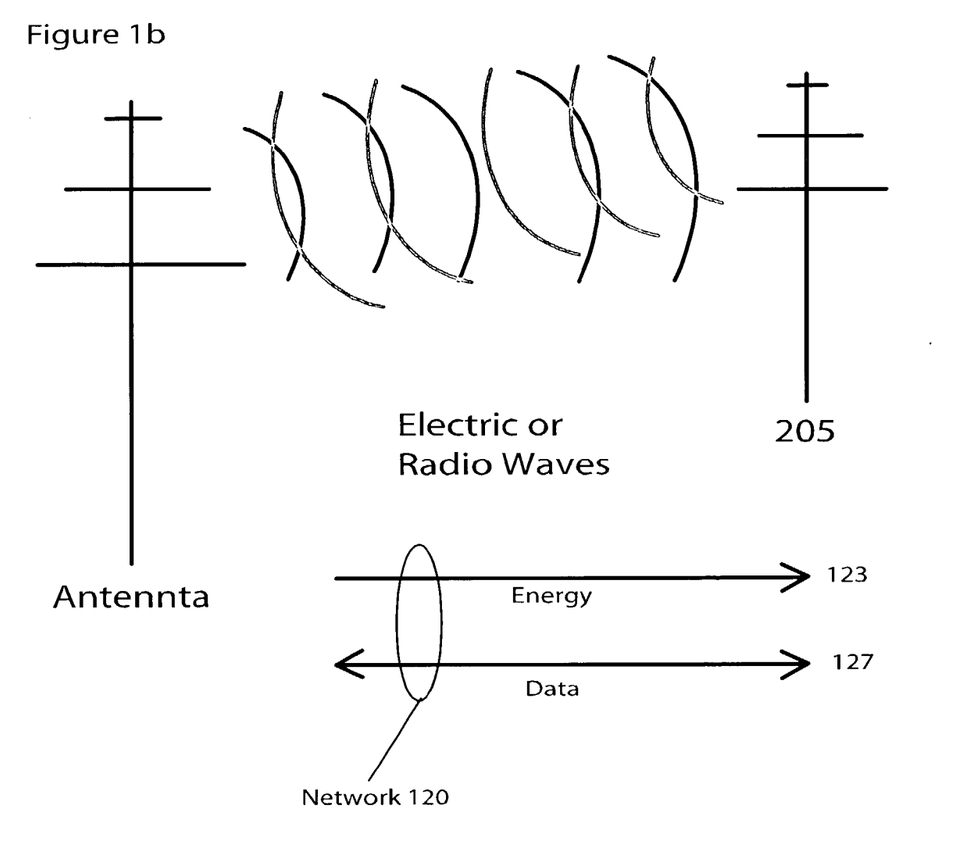
FIG. 1B is a diagram depicting the propagation coupling between two antennas.

FIG. 1B depicts an example of a propagating coupling otherwise known as electric coupling. The principles of the induction coupling described above, likewise apply to propagation coupling with the following principle difference: the propagation coupling uses electric frequency energy 205 instead of a magnetic field 105. This allows greater range for the transmissions as electric frequency energy can more readily be transmitted over greater distances than magnetic energy.

The RFE 123 transmitted by either of these methods is used in the present invention. These methods allow a primary transceiver to be in a sleeping condition; that is, not drawing power. This condition allows a device with power constraints to have an available a primary robust communication network that is powered down but is activated by the energy of a companion wireless system as described in FIGS. 1A and 1B.

Network 120 may be of a wide range of frequencies. For example, it may be low frequency such as 100–500 kHz, medium frequencies such as 10–15 MHz, or high frequencies such as 850 MHz, 2.4 GHz, or 5.8 GHz. In general, lower frequencies tend to have shorter ranges, slower data rates, and lower costs associated with devices. These specific frequencies are not meant to be exclusive or inclusive but are provided as examples.

Figure 2:
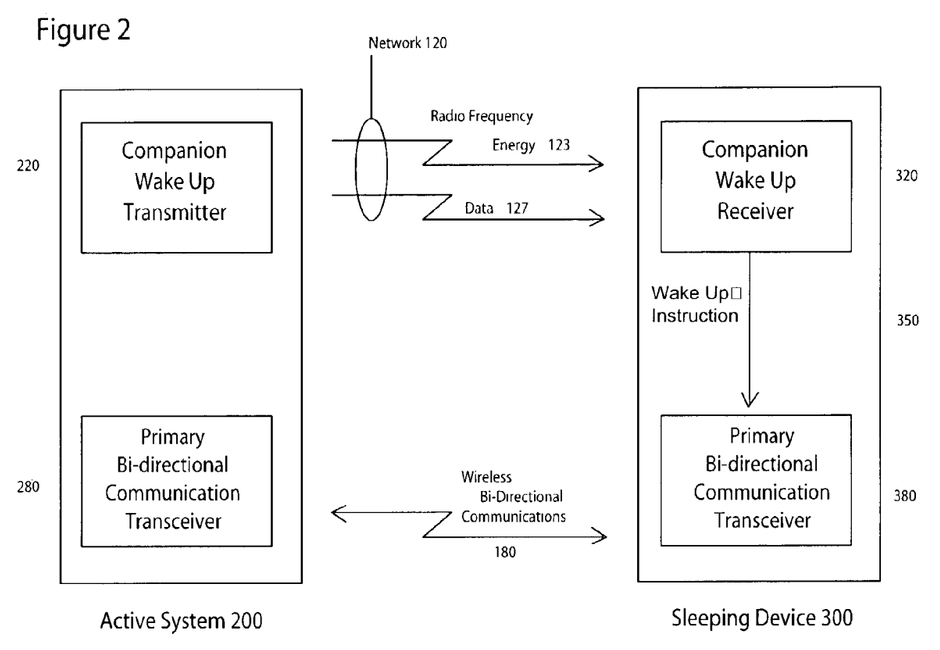
FIG. 2 is a block diagram depicting one embodiment of the present system.

FIG. 2 depicts an embodiment of the present invention. Depicted in FIG. 2 is a functional block diagram of components of the present communication system. An Active System 200 is depicted having two methods of transmission. We describe the System 200 as 'Active' because its wireless bi-directional communication transceiver (WBCT) 280 is powered up and ready to receive and transmit communications. In contrast, Sleeping Device 300 is described as 'Sleeping' because its primary WBCT 380 is not normally in a powered up state. Active System 200 uses a companion wake-up transmitter 220 to send RFE 123 to excite companion wake-up receiver 320. Wireless wake-up receiver 320 is excited by RFE 123 and activates WBCT 380. Now that it is activated, primary transceivers 280 and 380 establish communications 180.

Network 180 is a short-range, bi-directional, wireless network. Examples of network 180 include standard protocols such as Bluetooth, HomeRF, or WiFi (802.11). Or network 180 may be a proprietary standard.

It would be appreciated by one skilled in the art, that network 120 and network 180 might be in the same or different frequency bands. Likewise, wake-up transmitter 220 and wake up receiver 320 might be in the same or different frequency bands. For example, network 180 could be a network compatible with the Bluetooth protocol and network 120 might operate in the same or a nearby frequency band, around 2.4 GHz. Alternatively, network 180 may be of Bluetooth protocol, whereas network 120 might operate at a different frequency, for example, 850 MHz. It would be further appreciated by one skilled in the art, that wake-up transmitter 220 and transceiver 280 might share one or more components, such as the same antenna, the same exciters or transmitters and the same control circuits including processors and memory. In the same way, wake-up receiver 320 and transceiver 380 may share one or more components. Nevertheless, we can still refer to Device 300 as normally 'sleeping'. For example, if Sleeping Device 300 uses a Bluetooth protocol for its transceiver 380, it may normally keep the transceiver in a powered down condition and thus unable to receive Bluetooth transmissions. This is of advantage, because Bluetooth, which requires limited power compared with many short-range networks, requires relatively large power requirements compared with network 120. Reception can require more power than transmission in Bluetooth, whereas reception (and transmission) may require little or no power for receiver 320 besides the power received (RFE 123). However, RFE 123 may be received and activate the Bluetooth protocol in the transceiver or even activate power to other components of the device such as processors, sensors, or memory. Thus, Sleeping Device 300 may have a few or none of its subcomponents powered, and yet it can be externally activated by wake-up transmitter 220 and associated RFE 123. It would be further appreciated by one skilled in the art that transceivers functioning in different frequency bands and/or with different protocols can exist as distinct physical embodiments, or a single transceiver can function in multiple frequency bands with multiple protocols through the use of software alone or a combination of software and hardware. Thus, devices 200 and 300 may use distinct hardware and/or software to serve primary network 180 and companion network 120 or they may share hardware in serving the different networks.

Figure 3:
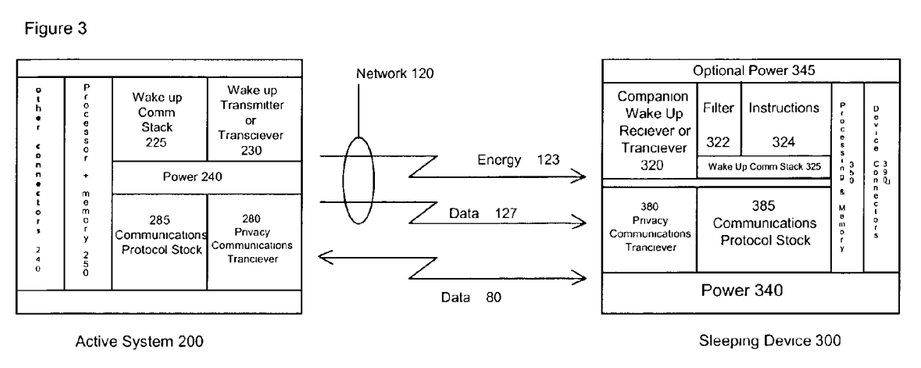
FIG. 3 is a block diagram depicting one embodiment of the present system.

FIG. 3 depicts a further embodiment of the present system. FIG. 3 is a block diagram depicting functional aspects of the present system. Companion wake-up transmitter 220 is preferably configured as a transceiver, and likewise is receiver 320 configured as a transceiver. Thus companion network 120 has full two-way data functionality. Transmissions from transceiver 320 to transceiver 220 may optionally be powered by energy 123 or supplemented by power source 345.

Transceiver 220 preferably includes data 127 in its communications to device 300. In one embodiment, this data includes an identifier code unique to device 300. Filter 322 compares the transmitted code to a stored code and if they match, activates further components of device 300. If the ID codes do not match no further action is taken. This aspect of the system allows device 300 to ignore spurious or unrelated energy 123.

In one embodiment, the data includes instructions to device 300. These instructions may include programming, tests, requests for specific responses through network 180 or network 120, instructions to process certain preprogrammed options, encrypted or non-encrypted security codes, or instructions related to device(s) connected at connection 390. Instructions are processed at module 324 which may or may not share processors or memory with device 300 located at module 350. In one embodiment, the communications network 180 cannot be established unless security protocols are first met by data transmitted in network 120. In one embodiment, network 120 is able to query status about device 300 or associated connections 390 when network 180 is not functioning. For example, power 340 may be a battery and it may be dead. Other types of troubleshooting or system status information may be provided.

In one embodiment, network 120 acts as a backup to network 180 if network 180 fails.

The processing of ID codes and instructions may be powered by RFE 123 or optional power 345. Power 345 may be the same or a different source as power 340.

In one embodiment, network 120 provides connection information to accelerate the link-up of network 180. For example, but without limitation, this data may include timing data, frequency hopping patterns, network protocols, etc.

Figure 4:
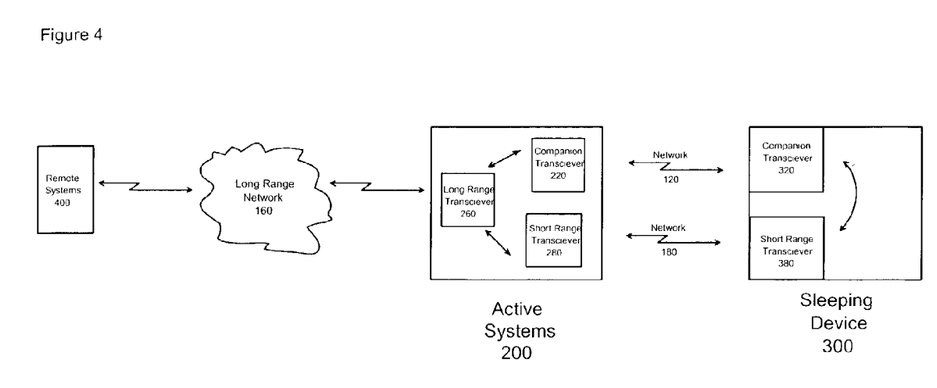
FIG. 4 is a block diagram depicting one embodiment of the present system.

FIG. 4 depicts a further embodiment of the present system. In this embodiment, active system 200 preferably includes a long-range, bi-directional transceiver 260. For example, this might be a transceiver compatible with cellular network protocols such as analog, ReFLEX, CDMA, GSM or others which are depicted as long-range network 160. (See further information on long-range bi-directional wireless networks included herein.) Long-range transceiver 260 is in communication with a remote system 400 through long-range network 160. Remote system 400 is able to be in communication with device 300 through the chain of network connections as depicted. If device 300 is 'sleeping', then remote system 400 sends a 'wake-up' and associated identification and instruction codes to system 200 through network 160 and associated transceiver 260. System 200 uses companion transceiver 220 to initiate communications with device 300 through network 120 and its associated transceivers 220 and 320. Once communications are initiated, full two-way communications are possible through long-range network 160 connected through primary network 180.

Figure 5:
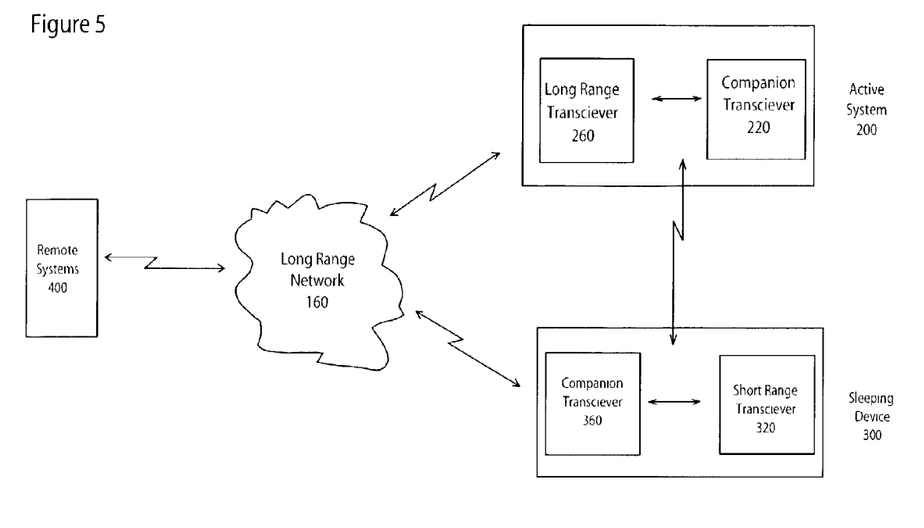
FIG. 5 is a block diagram depicting one embodiment of the present system.

FIG. 5 depicts a further embodiment of the present system. In this embodiment, sleeping device 300 preferable has a long-range bi-directional wireless transceiver 360 instead of a short-range transceiver as in the previous embodiment. However, as in the previous embodiment, remote system 400 initiates communication with device 300 through intermediary system 200 and companion network 120. Once communication is initiated, it is conducted without system 200, as device 300 has a long-range transceiver 360 and can connect more directly to system 400. Thus system 200 is used only as a 'wake-up', authorization, and instruction messenger to device 300.

About Data and Communication Protocols

Many data protocols are contemplated by the present invention. For example, such protocols include, without limitation, TCP/IP, ISDN, Bluetooth, CDMA/TDMA, Serial, synchronous/asynchronous, Wi/Fi, IEEE 802.15, etc. These protocols are described in more detail below.

About Short-Range Bi-Directional Networks

The figures illustrate communication across a short-range bi-directional wireless network 180 and related modules 280 and 380.

In one embodiment, the short-range wireless network utilizes a spread spectrum frequency hopping transceiver. This transceiver may communicate using a protocol compatible with BLUETOOTH®. BLUETOOTH® refers to a wireless, digital communication protocol using a low form factor transceiver that operates using spread spectrum frequency hopping at a frequency of around 2.45 GHz.

BLUETOOTH® is a trademark registered by Telefonaktiebolaget LM Ericsson of Stockholm, Sweden and refers to technology developed by an industry consortium known as the BLUETOOTH® Special Interest Group. BLUETOOTH® operates at a frequency of approximately 2.45 GHz, utilizes a frequency hopping (on a plurality of frequencies) spread spectrum scheme, and as implemented at present, provides a digital data transfer rate of approximately 1 Mb/second. Future implementations will include higher data transfer rates. In one embodiment, the present system includes a transceiver in compliance with BLUETOOTH® technical specification version 1.0, available at http://www-.bluetooth.com/dev/specifications.asp. In one embodiment, the present system includes a transceiver in compliance with standards established, or anticipated to be established, by the Bluetooth Special Interest Group.

In one embodiment, the present system includes a transceiver in compliance with standards established, or anticipated to be established, by the Institute of Electrical and Electronics Engineers, Inc., (IEEE). The IEEE 802.15 WPAN standard is anticipated to include the technology developed by the BLUETOOTH® Special Interest Group. WPAN refers to Wireless Personal Area Networks. The IEEE 802.15 WPAN standard is expected to define a standard for wireless communications within a personal operating space (POS) which encircles a person. The standard is available at http://grouper.ieee.org/groups/802/15.

In one embodiment, the transceiver includes a wireless, bi-directional, transceiver suitable for short-range, omnidirectional communication that allows ad hoc networking of multiple transceivers for purposes of extending the effective range of communication. Ad hoc networking refers to the ability of one transceiver to automatically detect and establish a digital communication link with another transceiver. The resulting network, known as a piconet, enables each transceiver to exchange digital data with the other transceiver. According to one embodiment, BLUETOOTH® involves a wireless transceiver transmitting a digital signal and periodically monitoring a radio frequency for an incoming digital message encoded in a network protocol. The transceiver communicates digital data in the network protocol upon receiving an incoming digital message.

According to one definition, and subject to the vagaries of radio design and environmental factors, short-range may refer to systems designed primarily for use in and around a premises and thus, the range generally is below a mile. Short-range communications may also be construed as point-to-point communications, examples of which include those compatible with protocols such as BLUETOOTH®, HomeRF™ (http://www.homerf.org), and the IEEE 802.11 WAN standard (http://grouper.ieee.org/groups/802/11). Long-range, thus, may be construed as networked communications with a range in excess of short-range communications. Examples of long-range communication may include, Aeris MicroBurst cellular communication system, and various networked pager, cellular telephone or, in some cases, radio frequency communication systems.

In the event that the present subject matter includes a transceiver compatible with BLUETOOTH® protocol, for example, then the device may have sufficient range to conduct bi-directional communications over relatively short-range distances, such as approximately 10 to 1,000 meters or more. In some applications, this distance allows communications throughout a premise.

The network module may include a separate, integrated or software based short-range bi-directional wireless module. The short-range network may be based upon HomeRF, 802.11, BLUETOOTH® or other conventional or unconventional protocols. However, these are short-range networks and the meaning imposed herein is to include premises and facility based wireless networks and not to describe long-range networks such as cellular telephone networks used to communicate over long distances. Such a system may include programmable or automatically selecting electronics to decide whether to conduct communications between the network module and an optional base station using the short-range module or the network module. In one embodiment the system may employ different portions of the network to provide short-range or long-range network connections, depending on the distance between the devices and the base stations. In one such embodiment, the network automatically adjusts for different required transmission distances.

In one embodiment, the transceiver is compatible with both a long-range communication protocol and a short-range communication protocol. For example, a person located a long distance away, such as several miles, may communicate with the transceiver using a cellular telephone compatible with the long-range protocol of transceiver.

Other short-range communication protocols are also contemplated and the foregoing examples are not to be construed as limitations but merely as examples.

About Long-Range Bi-Directional Networks

The figures depict the use of long-range bi-directional communication modules 260 and 360. For example, in one embodiment, long-range communication modules 260 and 360 include cellular telephone transceivers.

These long-range communications modules connect to a long-range, bi-directional network 160. Such a system incorporates an existing wireless communications network, such as a cellular network, satellite network, paging network, narrowband PCS, narrowband trunk radio, or other wireless communication network. Combinations of such networks and other embodiments may be substituted without departing from the present system.

In one embodiment, the long-range wireless network includes a cellular communications network. In one embodiment, the long-range wireless network includes a paging network. In one embodiment the long-range wireless network includes a satellite network. In one embodiment the long-range wireless network includes a wideband or narrowband PCS network. In one embodiment the long-range wireless network includes a wideband or narrowband trunk radio module. Other networks are possible without departing from the present system. In one embodiment, the network module supports multiple network systems, such as a cellular module and a two-way paging module, for example. In such embodiments, the system may prefer one form of network communications over another and may switch depending on a variety of factors such as available service, signal strength, or types of communications being supported. For example, the cellular network may be used as a default and the paging network may take over once cellular service is either weak or otherwise unavailable. Other combinations are possible without departing from the present system.

The long-range wireless network may include any consumer or proprietary network designed to serve users in range of the detection system, including, but not limited to, a cellular network such as analog or digital cellular systems employing such protocols and designs as CDPD, CDMA, GSM, PDC, PHS, TDMA, FLEX™, ReFLEX™, iDEN™, TETRA™, DECT, DataTAC™, and Mobitex™, RAM-NET™ or Ardis™ or other protocols such as trunk radio, Microburst™, Cellemetry™, satellite, or other analogue or digital wireless networks or the control channels or portions of various networks. The networks may be proprietary or public, special purpose or broadly capable. However, these are long-range networks and the meaning imposed herein is not to describe a premises or facility based type of wireless network.

The long-range wireless network may employ various messaging protocols. In one embodiment Wireless Application Protocol (WAP) is employed as a messaging protocol over the network. WAP is a protocol created by an international body representing numerous wireless and computing industry companies. WAP is designed to work with most wireless networks such as CDPD, CDMA, GSM, PDC, PHS, TDMA, FLEX, ReFLEX, iDEN, TETRA, DECT, DataTAC, and Mobitex and also to work with some Internet protocols such as HTTP and IP. Other messaging protocols such as iMode™, WML, SMS and other conventional and unconventional protocols may be employed without departing from the design of the present embodiment.

As an example, these long-range communication protocols described above may include, but are not limited to, cellular telephone protocols, one-way or two-way pager protocols, and PCS protocols. Typically, PCS systems operate in the 1900 MHZ frequency range. One example, known as Code-Division Multiple Access (CDMA, Qualcomm Inc., one variant is IS-95) uses spread spectrum techniques. CDMA uses the full available spectrum and individual messages are encoded with a pseudo-random digital sequence. Another example, Global Systems for Mobile communications (GSM), is one of the leading digital cellular systems and allows eight simultaneous calls on the same radio frequency. Another example, Time Division Multiple Access (TDMA, one variant known as IS-136) uses time-division multiplexing (TDM) in which a radio frequency is time divided and slots are allocated to multiple calls. TDMA is used by the GSM digital cellular system. Another example, 3G, promulgated by the ITU (International Telecommunication Union, Geneva, Switzerland) represents a third generation of mobile communications technology with analog and digital PCS representing first and second generations. 3G is operative over wireless air interfaces such as GSM, TDMA, and CDMA. The EDGE (Enhanced Data rates for Global Evolution) air interface has been developed to meet the bandwidth needs of 3G. Another example, Aloha, enables satellite and terrestrial radio transmissions. Another example, Short Message Service (SMS), allows communications of short messages with a cellular telephone, fax machine and an IP address. Messages typically have a length of 160 alpha-numeric characters. Another example, General Packet Radio Service (GPRS) is another standard used for wireless communications and operates at transmission speeds far greater than GSM. GPRS can be used for communicating either small bursts of data, such as e-mail and Web browsing, or large volumes of data.

In one embodiment, a long-range communication protocol is based on one way or two-way pager technology. Examples of one way pager protocols include Post Office Code Standardisation Advisory Group (POCSAG), Swedish Format (MBS), the Radio Data System (RDS, Swedish Telecommunications Administration) format and the European Radio Message System (ERMES, European Telecommunications Standards Institute) format, Golay Format (Motorola), NEC-D3 Format (NEC America), Mark IV/V/VI Formats (Multitone Electronics), Hexadecimal Sequential Code (HSC), FLEX™ (Motorola) format, Advanced Paging Operations Code (APOC, Philips Paging) and others. Examples of two-way pager protocols include ReFLEX™ (Motorola) format, InFLEXion (Motorola) format, NexNet (Nexus Telecommunications Ltd. of Israel) format and others.

Other long-range communication protocols are also contemplated and the foregoing examples are not to be construed as limitations but merely as examples.

About Basic Components

Devices 200 and 300 have basic components: processors, memory (RAM/ROM/EEPROM/DRAM/SRAM/DRIVES/etc), screens, input devices, microphones, speakers, vibrators, ports for data connections, (transceivers covered at length already), power supplies, etc. One of ordinary skill in the art will be aware of these and other basic components.

About the Active System

The active system 200 may be of several different designs. For example, in one embodiment it includes a response messaging capable two-way pager. This is a service where a two-way pager receives a message and optional multiple-choice responses. The user can select the appropriate responses. Such a design may be adapted to provide basic control options related to the system.

In one embodiment, the active system 200 includes a programmable two-way paging device such as the Motorola PageWriter™ 2000. This is a class of devices that acts as both a two-way pager and a handheld computer also known as a PDA (Personal Digital Assistant).

In one embodiment, the active system 200 includes a cellular telephone. The cell phone may be analog or digital in any of the various technologies employed by the cell phone industry such as PCS, or CDMA, or TDMA, or others. The cell phone may have programmable capability such as is found in a Nokia™ 9000 series of devices.

In embodiments where the user employs standard or adapted paging or cell phones as their active system 200, security passwords may be entered by using numeric or other keys on a phone. In one embodiment, the security password may be entered by speaking words. In this embodiment, the system may use word recognition, voice recognition or a combination of these technologies. In the embodiment of a pager, a distinct order of pressing certain keys could provide the equivalent of a security code. For example, 3 short and 1 long on a certain key; or once on key 'a', once on key 'b', and once more on key 'a'.

In one embodiment, the active system 200 includes a handheld computer. Some PDAs offer programmable capability and connectivity to various types of long-range wireless networks. An example of this type of device is the PalmPilot™ or Palm series of devices manufactured by 3-COM™. In these embodiments where a programmable active system 200 is used, such as a PalmPilot, PageWriter or programmable cell phone, the programmable nature of the devices facilitates the implementation of industry-standard designs and allows for the development of a program written for the devices.

In one embodiment, active system 200 is a handheld device running a version of Microsoft Windows® such as a Compaq IPAQ®.

In one embodiment, a special manufactured device may be manufactured to serve the needs of the system user.

In one embodiment, a special manufactured device is connected to an off the shelf hand-held device in order to deliver the preferred features of active system 200.

Alternative Embodiments and Networks Connected to the Active System 200

The active system 200 may include a first transceiver compatible with BLUETOOTH® or other short-range wireless network as described herein. Active system 200 may provide a repeater service to receive a message using BLUETOOTH® and to retransmit the message using a different communication protocol or also using BLUETOOTH® communication p brotocol.

Active system 200 may also include a second transceiver or a wired interface 260 having access to another communication network. The second transceiver or wired interface may retransmit the signal received from the device or received from some other device. In this way, central communication active system 200 may serve to extend the communication range of the device. For example, a message between the device and an emergency-dispatch center may be coupled to communication with the active system 200 connected network and a short-range wireless network. Communications between the present subject matter and a device coupled to communicate with the active system 200 connected network may be considered long-range communications.

Active system 200 may also communicate bi-directionally within the premise with one or more additional compatible devices. These may be a second device or any other device.

The active system 200 connected network 160 may be a public switched telephone network (PSTN), a pager communication network, a cellular communication network, a radio communication network, the Internet, or some other communication network. It will be further appreciated that with a suitable repeater, gateway, switch, router, bridge or network interface, the effective range of communication of a short-range transceiver may be extended to any distance. For example, active system 200 may receive transmissions on a BLUETOOTH® communication protocol and provide an interface to connect with the active system 200 connected network 160, such as the public switched telephone network (PSTN) using the active system 200 link. In this case, a wired telephone at a remote location can be used to communicate with the device. As another example, the range may be extended by coupling a BLUETOOTH® transceiver with a cellular telephone network, a narrow band personal communication systems (PCS) network, a CELLEMETRY® network, a narrow band trunk radio network or other type of wired or wireless communication network.

Examples of devices compatible with such long-range protocols include, but are not limited to, a telephone coupled to the public switched telephone network (PSTN), a cellular telephone, a pager (either one way or two-way), a personal communication device (such as a personal digital assistant, PDA), a computer, or other wired or wireless communication device.

In one embodiment, the network 160 may include a long-distance telephone network, which may include an intranet or the Internet. Coupling to such a network may be accomplished, for example, using a variety of connections, including a leased line connection, such as a T-1, an ISDN, a DSL line, or other high-speed broadband connection, or it may entail a dial-up connection using a modem. In one embodiment, the network 160 may include a radio frequency or satellite communication network. In addition, one or more of the aforementioned networks may be combined to achieve desired results.

Short-range communication protocols, compatible with the active system 200 may include, but are not limited to, wireless protocols such as HomeRF™, BLUETOOTH®, wireless LAN (WLAN), or other personal wireless networking technology. HomeRF™, currently defined by specification 2.1, provides support for broadband wireless digital communications at a frequency of approximately 2.45 GHz.

Other long-range and short-range communication protocols are also contemplated and the foregoing examples are not to be construed as limitations but merely as examples.

The active system 200 may be compatible with more than one communication protocol. For example, the active system 200 may be compatible with three protocols, such as a cellular telephone communication protocol, a two-way pager communication protocol, and BLUETOOTH® protocol. In such a case, a particular the device may be operable using a cellular telephone, a two-way pager, or a device compatible with BLUETOOTH®.

In one embodiment, the device can communicate with a remote device using more than one communication protocol. For example, the device may include programming to determine which protocol to use for communicating.

The determination of which communication protocol to use to communicate with a remote device may be based on power requirements of each transceiver, based on the range to the remote device, based on a schedule, based on the most recent communication from the remote device, or based on any other measurable parameter. In one embodiment, the device communicates simultaneously using multiple protocols.

In one embodiment, signals generated by the device are received by a central monitoring station. The central monitoring station may include operators that provide emergency dispatch services. An operator at the central monitoring station may also attempt to verify the authenticity of a received alarm signal. In one embodiment, the alarm signal generated by the device is first transmitted to a user, using either a short-range or long-range communication protocol, who then may forward the alarm signal to a monitoring station if authentic or cancel the alarm signal if the alarm is not valid.

In one embodiment, the device may communicate with a building control or security system by communicating using its transceiver. For example, the device may operate as an auxiliary input to a building control or security system. In which case, if the device detects a security event, by way of a sensor coupled to the device, then an alarm signal is transmitted from the device, via its transceiver, to the building security system. The building security system, if monitored by a central monitoring station, then forwards the alarm signal to the monitoring station. In one embodiment, the device can receive a transmission from a separate building control or security system. If the building security system detects an alarm condition, then the security system can, for example, instruct the device to repeatedly toggle power to load a flashing light visible from the exterior of the building may aid emergency personnel in locating an emergency site. Alternatively, the device can establish communications with a predetermined remote device or a central monitoring service.

In one embodiment, there are various types of networks connected to the active system 200. These may be telephone networks, modem connections, frame relay systems, spread-spectrum, DSL, cable modems, dedicated line or other similar wire based communication and data networks. In addition, these may be long-range, bi-directional, wireless networks as describe above.

In one embodiment, there is a connection to the Internet using various Internet protocols such as TCP/IP/HTTP/HTCP and others.

In addition, feedback may be transmitted to a remote device based on the operation of the device. For example, if a user issues a command to the device using the cellular telephone, then the display of the phone will indicate the changes arising from the command. In one embodiment, the cellular telephone, the active system 200, emergency monitoring center, or other device, displays real time information from the device.

Various methods may be used to communicate with, or send a message or instruction to, the device from a remote location. For example, using a cellular telephone, a user may speak a particular phrase, word or phoneme that is recognized by the cellular telephone which then generates and transmits a coded message to the device. As another example, the user may manipulate a keypad on the telephone to encode and transmit a message to the device.

In one embodiment, there are multiple destinations for the transmitted information. This may include a active system 200 (at a home), multiple cell phones (or other network devices—for example, to notify a parent of the use of the device) or an emergency-dispatching center.

About the Sleeping Device

In certain embodiments, the sleeping device 300 may take a wide variety of physical forms, shapes, sizes, and protective housings to meet the application requirements. They may be similar in shape to a grain of rice, a pencil lead, a match, a stamp, etc. They may be inserted beneath the skin, dispersed in the environment, attached to structures, flow in fluid within a pipe or in a tank, attached to other devices, integrated in the circuit of another system, etc. They may be designed to withstand a wide variety of environmental conditions such as temperature, humidity, exposure to chemicals, shock, vibration, etc.

In certain embodiments, sleeping device 300 often acts as the interface between the physical world and electronic world. Therefore it is often associated with sensors of various types; for example, temperature, humidity, chemical agents, biological agents, light, vibration, location technologies such as GPS, loran, etc., bodily functions such as respiration, heartbeat, blood chemistry, brainwaves, etc.

The sleeping device 300 may, for example, be implemented as an extension to a Radio Frequency Identification (RFID) tag. An RFID tag is, typically, a small, battery-free transponder. When the transponder is to be read, a reading device sends out a radio frequency power pulse to the antenna of the transponder, which is tuned to the same frequency as the reader. The magnetic field generated by the reader is collected by the transponder's antenna, rectified, and stored on a small capacitor within the transponder. When the power pulse has finished, the transponder immediately transmits back its data, using the energy stored within its capacitor as its power source. Thus, the RFID transponder is powered-off, or sleeping, until it is woken up by the radio frequency signal from the reading device.

EXAMPLES OF EMBODIMENTS

In a first embodiment, the sleeping device 300 may be incorporated into a sensor of a security system, for example, a glass breakage sensor. To conserve power, the sensor's wireless communications transceiver 380 is normally powered down, while the sensor itself and its processor draw enough power to respond to a breakage event. Upon detecting glass breakage, the sensor/processor module can power up the wireless communications transceiver 380 and use it to transmit signals associated with the detected event to a central control panel. In addition, the central control panel may query the sensor as to its status by sending a wake-up signal to the sensor's wake-up receiver 320. When the wake-up receiver 320 detects the radio frequency energy of the query, the receiver 320 can power up the wireless communications transceiver 380, which can then send status data to the central control panel.

In a second embodiment, the sleeping device 300 may be incorporated into an implanted medical device such as a combination heart monitor/defibrillator that is implanted in a person's body. The monitor/defibrillator draws enough power to monitor the heartbeat and to respond to fibrillation by beginning defibrillation, but the monitor/defibrillator's wireless communications transceiver 380 is normally powered down to conserve power. However, the battery of the monitor/defibrillator has a limited lifetime, and it is necessary for a medical professional to query the status of the battery periodically. To avoid subjecting the patient to additional surgery, a reading device may send a wake-up signal to the wake-up receiver 320 of the sleeping device 300. The receiver 320 can then power up the wireless communications transceiver 380, which in turn can send data on the battery's charge to the reading device. Similar processes can be used to read electrocardiogram signals, program the device, or send or receive other data related to the device.

CONCLUSION

Other embodiments are possible and the examples provided herein are intended to be demonstrative and not exclusive or exhaustive of the present invention, which is determined by the scope of the appended claims and the full range of equivalents to which they are entitled.

What is claimed is:

1. A wireless communications apparatus, comprising:
 (a) a wake-up receiver adapted to receive a wake-up signal over a secondary network;
 (b) an initially powered-off, sleeping wireless communications transceiver communicating over a primary network and adapted to be powered on by the wake-up receiver when the wake-up receiver receives the wake-up signal;
 (c) wherein the wake-up receiver receives data other than the wake-up signal; and
 (d) wherein the data is an activation signal causing the secondary network to take over the function of the primary network.

2. The apparatus of claim 1, wherein the wake-up receiver only draws power from the wake-up signal.

3. The apparatus of claim 1, wherein the wake-up receiver and the powered-off, sleeping wireless communications transceiver share components.

4. The apparatus of claim 1, wherein the primary network and the secondary network use the same frequency band.

5. The apparatus of claim 1, wherein the primary network and the secondary network use different frequency bands.

6. The apparatus of claim 1, wherein the secondary network is bi-directional, the wake-up receiver being a transceiver.

7. The apparatus of claim 1, wherein the wake-up receiver is powered by a power source distinct from that powering the wireless communications transceiver.

8. The apparatus of claim 1, wherein the data is an identification code, and further comprising a filter comparing the received identifier code to a stored code.

9. The apparatus of claim 8, wherein components associated with the sleeping wireless communications transceiver are activated if the identifier code matches the stored code.

10. The apparatus of claim 1, wherein the data is a security protocol governing the activation of the primary network.

11. The apparatus of claim 1, wherein the data is a query to the sleeping wireless communications transceiver, which returns a response to the query.

12. The apparatus of claim 1, wherein the secondary network utilizes a magnetic signal.

13. The apparatus of claim 1, wherein the secondary network utilizes a radio frequency signal.

14. The apparatus of claim 1, wherein the secondary network utilizes short-range data communications protocols.

15. The apparatus of claim 14, wherein the short-range data communications protocols are selected from the group consisting of Bluetooth™, HomeRF™, IEEE 802.15, and IEEE 802.11.

16. The apparatus of claim 1, wherein the primary network utilizes short-range data communications protocols.

17. The apparatus of claim 16, wherein the short-range data communications protocols are selected from the group consisting of Bluetooth™, HomeRF™, IEEE 802.15, and IEEE 802.11, an ad hoc networking.

18. The apparatus of claim 1, further comprising a long-range bi-directional transceiver associated with the sleeping wireless communications transceiver.

19. The apparatus of claim 18, further comprising a remote system communicating with the long-range bi-directional transceiver over a long-range network.

20. The apparatus of claim 19, wherein the long-range network utilizes communications protocols selected from the group consisting of CDPD, CDMA, GSM, 3G, WAP, Aloha, PDC, PHS, PCS, trunk radio, TDMA, FLEX™, ReFLEX™, iDEN™, TETRA™, DECT, DataTAC™, Mobitex™, RAMNET™, and Ardis™.

21. The apparatus of claim 19, wherein the long-range network utilizes communications protocols selected from the group consisting of POCSAG, MBS, RDS, ERMES, Golay Format, NEC-D3 Format, Mark IV/V/VI Formats, Hexadecimal Sequential Code, FLEX™ format, Advanced Paging Operations Code, ReFLEX™ format, inflexion format, and NexNet format.

22. The apparatus of claim 1, where the data comprises connection information to accelerate the activation of the sleeping wireless communications transceiver to communicate with other systems.

23. The apparatus of claim 22, where the data is selected from the group consisting of timing data, frequency hopping patterns, and network protocols.

* * * * *